United States Patent [19]

Albert et al.

[11] 4,363,918

[45] Dec. 14, 1982

[54] METHOD OF PREPARING 1-ALKYL-3-CARBOXY-1H PYRROLE-2-ACETIC ACIDS

[75] Inventors: Rudolf Albert, Mechelen; Albert Willemsens, Beerse; Guido van der Veken, Turnhout, all of Belgium

[73] Assignee: Janssen Pharmaceutica N.V., Beerse, Belgium

[21] Appl. No.: 230,784

[22] Filed: Feb. 2, 1981

Related U.S. Application Data

[63] Continuation of Ser. No. 74,447, Sep. 11, 1979, abandoned, which is a continuation of Ser. No. 918,855, Jun. 23, 1978, abandoned.

[51] Int. Cl.$^3$ .................................. C07D 207/34
[52] U.S. Cl. ....................................... 548/531
[58] Field of Search ................................... 260/326.46

[56] References Cited

U.S. PATENT DOCUMENTS

| | | | |
|---|---|---|---|
| 3,752,826 | 8/1973 | Carson | 424/274 |
| 3,865,840 | 2/1975 | Carson | 260/326.46 |
| 3,952,012 | 4/1976 | Carson | 260/326.46 |
| 4,048,191 | 9/1977 | Carson | 260/326.46 |

*Primary Examiner*—Mary C. Lee
*Attorney, Agent, or Firm*—Geoffrey G. Dellenbaugh

[57] ABSTRACT

An improved method of preparing 1-alkyl-3-carboxy-1H-pyrrole-2-acetic acids, the latter compounds being useful intermediates in the preparation of certain anti-inflammatory 1H-pyrrole-2-acetic acids.

8 Claims, No Drawings

METHOD OF PREPARING 1-ALKYL-3-CARBOXY-1H PYRROLE-2-ACETIC ACIDS

This is a continuation, of application Ser. No. 74,447, filed Sept. 11, 1979 now abandoned which in turn is a continuation/Appln. Ser. No. 918,855, filed June 23, 1978, now abandoned.

DESCRIPTION OF THE INVENTION

The present invention is concerned with the preparation of certain 1-alkyl-3-carboxy-1H-pyrrole-2-acetic acids which may structurally be represented by the formula

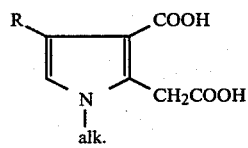

wherein R is a member selected from the group consisting of hydrogen and lower alkyl; and alk represents a lower alkyl radical.

As used herein "lower alkyl" is meant to include straight and branched hydrocarbon radicals having from 1 to about 6 carbon atoms such as, for example, methyl, ethyl, 1-methylethyl, 1,1-dimethylethyl, propyl, butyl, pentyl, hexyl and the like.

The subject compounds of formula (I) are described in U.S. Pat. Nos. 3,752,826, 3,865,840, and 3,952,012 as useful intermediates for the preparation of certain 5-aroyl-1H-pyrrole-2-acetic acids with valuable anti-inflammatory activities. Specific well-known anti-inflammatory agents which may advantageously be prepared starting from compounds of formula (I) include 1-methyl-5-(4-methylbenzoyl)-1H-pyrrole-2-acetic acid, generically designated as tolmetin, and, 5-(4-chlorobenzoyl)-1,4-dimethyl-1H-pyrrole-2-acetic acid, generically designated as zomepirac.

According to the above-indicated U.S. Patents the desired anti-inflammatory 5-aroyl-1H-pyrrole-2-acetic acids can be prepared by carrying out the steps of:

(i) reacting an appropriate 1-chloro-2-alkanone of formula (II) with a mixture of an appropriate di(lower alkyl)3-oxo-pentanedioate of formula (III) and a lower alkanamine (IV), preferably in an aqueous medium, to obtain a di-ester of the formula (V);

(ii) hydrolizing said (V) to obtain the corresponding acid of formula (I);

(iii) partially esterifying the latter with an acidic solution of a lower alkanol to yield the corresponding alkyl 1-alk-3-carboxy-1H-pyrrole-2-acetate (VI);

(iv) decarboxylating (VI) by heating it in an inert atmosphere or in a suitable basic solvent such as quinoline;

(v) subjecting the thus obtained (VII) to a Friedel-Crafts reaction with an appropriate aroylhalide (VI), yielding an alkyl 5-aroyl-1H-pyrrole-2-acetate of the formula (VIII); and (vi) finally hydrolyzing said (VIII) to obtain the desired acid of formula (IX).

The foregoing reactions are illustrated as follows

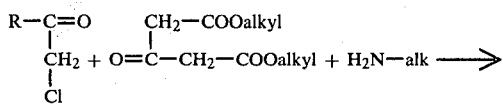

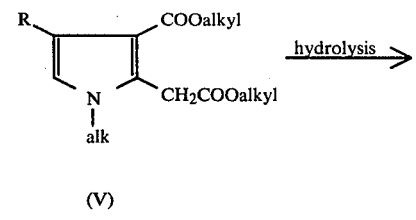

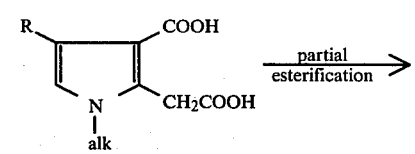

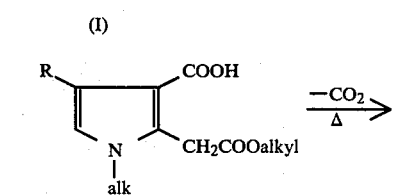

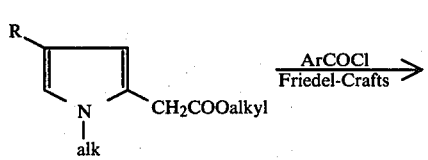

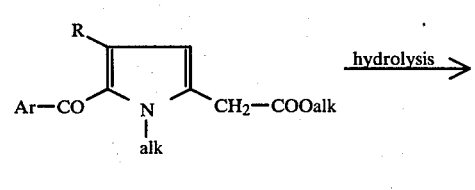

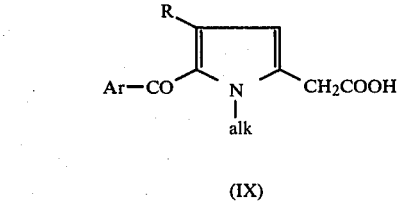

In the foregoing formulae Ar represents an aromatic radical selected from the group consisting of phenyl, thienyl, 5-methyl-2-thienyl and substituted phenyl, said substituted phenyl having from 1 to 3 substituents independently selected from the group consisting of halo, lower alkyl, trifluoromethyl, lower alkyloxy, nitro, amino, cyano and methylthio.

Although the feasibility of the foregoing reaction sequence has been proven, the method was nevertheless not quite satisfactory. In particular, in the preparation of the di-acids (I) starting from (II), (III) and (IV) only low yields could be achieved.

It has now, quite unexpectedly, been found that the di-acids of formula (I) can conveniently be obtained in one step and with a high yield by the reaction of a 1-chloro-2-alkanone of formula (II) with 3-oxo-pentanedioic acid (X) and a lower alkanamine (IV).

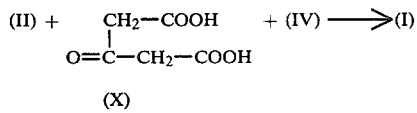

The preparation of (I) starting from (II), (X) and (IV) is preferably carried out in an aqueous medium at a temperature which is low enough to avoid decomposition of the 3-oxo-pentanedioic acid. Advantageously the reaction mixture is kept well below room temperature and preferably at about 0° C. or at an even lower temperature. In a preferred method of operating a solution of (X) in water is first cooled to below 0° C. Then there is added slowly the amine (IV) while continuously cooling.

Subsequently the ketone of formula (II) is added in small portions. An exothermic reaction takes place and vigorous cooling is appropriate to keep the temperature below 15°–20° C. The reaction mixture is further stirred for several hours at a temperature of about 0° C. whereafter the formed product is precipitated by pouring the reaction mixture in ice-hydrochloric acid.

In comparison with the prior art method, the method of the present invention is far superior. Not only is there eliminated one step, more particularly the hydrolysis-step, but, in addition, substantially higher yields can be obtained. Whereas in the previously known method overall yields of about 40 to 50% only were achieved for the preparation of (I) starting from (II), (III) and (IV), yields obtained with the present method may be 85% and even higher.

Isolation of the di-acid of formula (I) from the reaction mixture is simple, i.e. by adding acid and filtering off the precipitated product. The product abtained has a high degree of purity. Alkylamides, which are normally formed as side-products in the prior art method, and which can only be eliminated with difficulty, are not produced.

An additional, economical, advantage of the present method is that the 3-oxo-pentanedioic acid of formula (X) which is used as a starting material herein is less expensive than the corresponding di-esters of formula (III) which are normally prepared by esterifying the corresponding di-acid (X).

In view of the foregoing, the present invention provides a noticeable enrichment of the art.

The invention is further illustrated and not limited by the following examples. Unless otherwise stated all parts therein are by weight.

EXAMPLE 1

To 1200 parts of cold water (about 5° C.) there are added 292 parts of 3-oxo-pentanedioic acid and the reaction mixture is further cooled to −5° C. 1770 Parts of methanamine 35% in water are then added slowly while stirring and cooling to a temperature between −5° C. and 5° C. The reaction mixture is further cooled to about −15° C. Then 370 parts of 1-chloro-2-propanone are added portionwise under vigorous cooling. An exothermic reaction takes place and the temperature of the mixture raises to about 15° C. It is again cooled to about 0° C. and further stirred at this temperature for about 16 hours. The reaction mixture is then poured onto a mixture of 4000 parts of ice and 2200 parts of concentrated hydrochloric acid solution (10.5 N) and stirring is continued for 20 minutes. The product is filtered off and dried in vacuo at 50° C. over $CaCl_2$, yielding 335 parts (85%) of 3-carboxy-1,4-dimethyl-1H-pyrrole-2-acetic acid, mp. 192.8°–194.6° C. dec.

EXAMPLE II

Following the procedure of Example I and using equivalent amounts of the appropriate starting materials there are also obtained:
3-carboxy-1-methyl-1H-pyrrole-2-acetic acid; and
3-carboxy-1-ethyl-4-methyl-1H-pyrrole-2-acetic acid.

What we claim is:

1. A process of preparing 1-alkyl-3-carboxy-1H-pyrrole-2-acetic acids having the formula

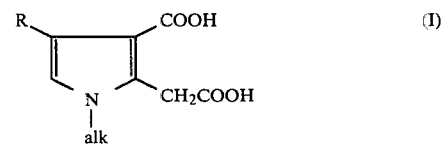

wherein R is a member selected from the group consisting of hydrogen and lower alkyl and alk represents a lower alkyl radical, which process comprises a condensation reaction of 3-oxo-pentanedioic acid with a 1-chloro-2-alkanone of the formula

and a lower alkanamine.

2. A process of preparing 3-carboxy-1,4-dimethyl-1H-pyrrole-2-acetic acid which comprises a condensation reaction of 3-oxo-pentanedioic acid with 1-chloro-2-propanone and methanamine.

3. A process of preparing a 1-alkyl-3-carboxy-1H-pyrrole-2-acetic acid having the formula:

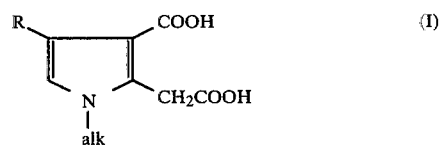

wherein R is a member selected from the group consisting of hydrogen and loweralkyl and alk represents a loweralkyl radical, which process comprises:
 (a) slow addition of a loweralkanamine to an aqueous solution of 3-oxo-pentanedioic acid previously cooled to below about 0° C., with continuous cooling of the resulting mixture;
 (b) addition of said mixture of small portions of 1-chloro-2-alkanone of formula

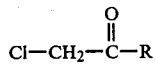

with vigorous cooling to maintain the temperature of the reaction mixture below 20° C.; and (c) stirring the resulting reaction mixture for several hours at a temperature of about 0° C.

4. The process of claim 3 in which the temperature in step (b) is maintained below 15° C.

5. A process according to claim 1 wherein said condensation reaction is carried out in an aqueous medium.

6. A process according to claim 5 wherein said condensation reaction is carried out at a temperature below 20° C.

7. A process according to claim 2 wherein said condensation reaction is carried out in an aqueous medium.

8. A process according to claim 7 wherein said condensation reaction is carried out at a temperature below 20° C.

* * * * *